United States Patent
Wang et al.

(10) Patent No.: US 10,870,610 B2
(45) Date of Patent: *Dec. 22, 2020

(54) PRODUCTION OF NEOPENTANE

(71) Applicant: ExxonMobil Chemical Patents Inc., Baytown, TX (US)

(72) Inventors: Kun Wang, Bridgewater, NJ (US); Lorenzo C. DeCaul, Langhorne, PA (US); Steven W. Levine, Hopewell, NJ (US); Etienne Mazoyer, Woluwe Saint Pierre (BE); James R. Lattner, La Porte, TX (US); Helge Jaensch, Grimbergen (BE); Ali A. Kheir, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 128 days.

This patent is subject to a terminal disclaimer.

(21) Appl. No.: 16/324,788

(22) PCT Filed: Aug. 18, 2017

(86) PCT No.: PCT/US2017/047596
§ 371 (c)(1),
(2) Date: Feb. 11, 2019

(87) PCT Pub. No.: WO2018/044596
PCT Pub. Date: Mar. 8, 2018

(65) Prior Publication Data
US 2019/0225561 A1   Jul. 25, 2019

Related U.S. Application Data

(60) Provisional application No. 62/380,520, filed on Aug. 29, 2016.

(30) Foreign Application Priority Data

Oct. 21, 2016   (EP) .................................. EP16194988

(51) Int. Cl.
*C07C 2/58* (2006.01)
*C07C 4/10* (2006.01)
(Continued)

(52) U.S. Cl.
CPC .................. *C07C 2/56* (2013.01); *C07C 2/58* (2013.01); *C07C 4/06* (2013.01); *C07C 4/10* (2013.01);
(Continued)

(58) Field of Classification Search
None
See application file for complete search history.

(56) References Cited

U.S. PATENT DOCUMENTS 2,267,730 A * 12/1941 Grosse ...................... C07C 2/62
585/723
2,325,052 A    7/1943 Grosse et al.
(Continued)

FOREIGN PATENT DOCUMENTS

GB    574694    1/1946
GB    1220015   4/1967
(Continued)

OTHER PUBLICATIONS

Clarke et al., "The Preparation and Activity for Alkane Reactions of Aerosil-Supported Rhodium-Copper Clusters," Journal of Catalysis, vol. 111, pp. 374-382 (1988).
(Continued)

*Primary Examiner* — Philip Y Louie

(57) ABSTRACT

Disclosed herein are processes for producing neopentane. The processes generally relate to demethylating isooctane to
(Continued)

produce neopentane. The isooctane may be provided by the alkylation of isobutane with butylenes.

19 Claims, 2 Drawing Sheets

(51) Int. Cl.
      *C07C 2/56*       (2006.01)
      *C07C 4/06*       (2006.01)
      *C09K 5/08*       (2006.01)
      *C08J 9/00*       (2006.01)
      *C10L 1/04*       (2006.01)
      *C08J 9/14*       (2006.01)
      *C09K 5/00*       (2006.01)
(52) U.S. Cl.
      CPC ............ *C08J 9/0014* (2013.01); *C08J 9/141* (2013.01); *C09K 5/08* (2013.01); *C10L 1/04* (2013.01); *C07C 2521/08* (2013.01); *C07C 2523/46* (2013.01); *C07C 2523/58* (2013.01); *C07C 2523/755* (2013.01); *C09K 5/00* (2013.01)

(56) References Cited

U.S. PATENT DOCUMENTS

| | | | |
|---|---|---|---|
| 2,394,743 | A | 2/1946 | Bergsteinsson |
| 2,413,691 | A | 1/1947 | Crawford et al. |
| 2,422,670 | A | 6/1947 | Haensel et al. |
| 2,422,672 | A | 6/1947 | Haensel et al. |
| 2,422,674 | A | 6/1947 | Haensel et al. |
| 2,422,675 | A | 6/1947 | Haensel et al. |
| 2,436,695 | A * | 2/1948 | Kuhn, Jr. ................. C07C 2/62 585/710 |
| 2,436,923 | A | 3/1948 | Haensel et al. |
| 3,585,252 | A | 6/1971 | Kennedy |
| 3,660,516 | A | 5/1972 | Crain et al. |
| 3,755,493 | A | 8/1973 | Norel |
| 3,855,346 | A | 12/1974 | Norel |
| 4,593,147 | A | 6/1986 | Butter et al. |
| 4,940,829 | A | 7/1990 | Drake |
| 5,146,037 | A | 9/1992 | Zarchy et al. |
| 5,481,057 | A * | 1/1996 | Bell .......................... C07C 2/58 585/314 |
| 6,262,192 | B1 | 7/2001 | Wu |
| 2007/0043247 | A1 | 2/2007 | Webber et al. |

FOREIGN PATENT DOCUMENTS

| | | |
|---|---|---|
| WO | 2018/044591 | 3/2018 |
| WO | 2018/044592 | 3/2018 |
| WO | 2018/044596 | 3/2018 |

OTHER PUBLICATIONS

Haensel et al., "Selective Demethylation of Paraffin Hydrocarbons: Preparation of Triptane and Neopentane," Industrial and Engineering Chemistry, vol. 39, pp. 853-857 (1947).
Foger et al., "Skeletal Reactions of Hydrocarbons over Supported Iridium-Gold Catalysts," Journal of Catalysis, vol. 64, pp. 448-463 (1980).
Vogelzang et al., "Reactions of 2,2-Dimethylbutane on Iridium: The Role of Surface Carbonaceous Layers and Metal Particle Size," Journal of Catalysis, vol. 111, pp. 77-87 (1988).
Machiels, et al., "Hydrogenolysis of 2,2-Dimethylbutane and n-Hexane over Supported Ruthenium, Nickel, Cobalt, and Iron," Journal of Catalysis, vol. 58, pp. 268-275 (1979).
Leclercq et al., "Hydrogenolysis of Saturated Hydrocarbons: Influence of Hydrocarbon Structures on the Activity and Selectivity of Nickel on Silica," Journal of Catalysis, vol. 99, pp. 1-11 (1986).
Birkhoff et al., "NExOCTANETM Technology for Isooctane Production," in Handbook of Petroleum Refining Processes, Third Edition, Ch. 1.1 (2004).
Kranz, K., "Alkylation chemistry-Mechanism, operating variables, and olefin interactions", DuPont Company, 2003.
Zimmer, H. et al., "Hydrogenolysis of alkanes with quaternary carbon atoms over Pt and Ni black catalysts", J.Chem. Soc., Fararday Trans. 1, 1982.
Graves, "SRATCO Effluent Refrigerated H2SO4 Alkylation Process," in Handbook of Petroleum Refining Processes, Third Edition, ch. 1.2 (2004).
Roeseler, "UOP AlkyleneTM Process for Motor Fuel," in Handbook of Petroleum Refining Processes, Third Edition, ch. 1.3 (2004).
Himes et al., "UOP HF Alkylation Technology," in Handbook of Petroleum Refining Processes, Third Edition, ch. 1.2 (2004).
Cusher, "UOP Penex Process," Handbook of Petroleum Refining Processes, Third Edition, Ch. 9.3 (2004).
Matsumoto et al., "Contrast between nickel and platinum catalysts in hydrogenolysis of saturated hydrocarbons," Journal of Catalysis, vol. 19(2), p. 101 (1970).
Matsumoto et al., "The classification of metal catalysts in hydrogenolysis of hexane isomers," Journal of Catalysis, vol. 22, pp. 182-192 (1971).
Paál et al, "On the pattern of hydrogenolysis of hexane isomers over four Group VIIIB metals," Reaction Kinetics and Catalysis Letters, vol. 12(2), pp. 131-137 (1979).
Richardson J. et al , "Preparation variables in nickel catalysts", J. Catal. 54, 207-218, 1978.
Schepers F.J., "Apparent particle size sensitivity in hydrocarbon reactions, "J. Catal. 96, 82-87, 1985.
Richardson J. et al., "Crystallite Size Distributions and Stabilities of Homogeneously Deposited Ni/SiO2 Catalysts," Stu. Surf. Sci. Catal. 3, 131-142, 1979.
Coenen J., "Catalytic hydrogenation of fatty oils," Ind. Eng. Chem. Fundamen. 25 (1) 43-52, 1986.
Song C. et al., "Properties of the Ni/Kieselguhr catalysts prepared by precipitation method," Korean J. of Chem. Eng. 9 (3) 159-163, 1992.
Mendioroz S. et al., "Effect of the method of preparation on the activity of nickel Kieselguhr catalyst for vegetable oil hydrogenation," Appl. Catal. 66, 73-90, 1990.
Hadley, G.R., "Thermal conductivity of packed metal powders," International Journal of Heat and Mass Transfer 29.6, 909-920, 1986.
Avdonina, E.N., "Reactions of tritium recoil atoms in liquid mixtures of isooctane with benzene," XP002768312 & vol. 15, No. 5, 1973, pp. 720-726.
Zidek, Zdeno et al., "Nickel-silica-alumina catalysts. III. Catalytic properties. Hydrocracking of isooctane", 1969.
Seth et al., "Selective hydrogenation of 1,3-butadiene in mixture with isobutene on a Pd/@a-alumina catalyst in a semi-batch reactor", vol. 62, No. 17, (2007).

* cited by examiner

PRODUCTION OF NEOPENTANE

CROSS REFERENCES TO RELATED APPLICATIONS

This invention is a National Phase Application claiming priority to PCT Application Serial No. PCT/US2017/047596 filed Aug. 18, 2017, which claims priority to and benefit of U.S. Ser. No. 62/380,520, filed Aug. 29, 2016 and EP 16194988.8, filed Oct. 21, 2016, the disclosures of which are incorporated by reference.

FIELD OF INVENTION

The present invention relates to methods of producing neopentane and uses thereof.

BACKGROUND OF INVENTION

Neopentane is a unique nonpolar hydrocarbon molecule that has found industrial use in the form of an inert condensing agent for gas-phase reactions. See, for instance, U.S. Pat. No. 6,262,192. Other potential industrial uses for neopentane include use as a heat removal agent, a blowing agent, and a gasoline blend component due to its relatively high octane numbers. For instance, neopentane has a Research Octane Number (RON) of 85.5 and a Motor Octane Number (MON) of 80.2.

Currently, there is no satisfactory process for producing neopentane on a commercial scale. For example, typical existing processes for synthesizing neopentane utilize stoichiometric reactions of t-butylchloride and a Grignard reagent, methyl aluminum dichloride, dimethyl aluminum chloride, or trimethyl aluminum. See, for instance, U.S. Pat. No. 3,585,252. Such stoichiometric reactions generate large amounts of metal halides and are difficult to scale up to produce neopentane at commercial quantities. Likewise, though neopentane may be synthesized by hydrogenation of neopentanoic acid under high pressure and at high temperature, e.g., as described in U.S. Pat. No. 4,593,147, such processes are expensive due to the neopentanoic acid feedstock and suffer from a combination of demanding reaction conditions and low selectivity.

Other proposed processes for producing neopentane involve demethylation of higher carbon number branched paraffins. For example, U.S. Pat. Nos. 4,940,829 and 2,422,675 each relate to the preparation of neopentane via catalytic demethylation of neohexane. However, these higher carbon number branched paraffins are not readily available in high concentrations suitable as feedstock that could be utilized on a commercial scale.

Yet alternatively, a process for producing neopentane by hydrogenating an isobutylene polymer and selectively cracking the hydrogenation product is described in U.S. Pat. No. 2,394,743. However, in addition to producing neopentane, this process also produces large amounts of heavier hydrocarbon components.

Thus, there remains a need for processes for producing neopentane at high yield under mild reaction conditions and utilizing low cost, readily available feedstock. Such processes would allow economic production of neopentane at commercial quantities.

Other references of interest include: "The Preparation and Activity for Alkane Reactions of Aerosil-Supported Rhodium-Copper Clusters," Clarke et al., *Journal of Catalysis*, vol. 111, pp. 374-82 (1988); "Selective Demethylation of Paraffin Hydrocarbons: Preparation of Triptane and Neopentane," Haensel et al., *Industrial and Engineering Chemistry*, vol. 39, pp. 853-57 (1947); "Skeletal Reactions of Hydrocarbons over Supported Iridium-Gold Catalysts," Foger et al., *Journal of Catalysis*, vol. 64, pp. 448-63 (1980); "Reactions of 2,2-Dimethylbutane on Iridium: The Role of Surface Carbonaceous Layers and Metal Particle Size," Vogelzang et al., *Journal of Catalysis*, vol. 111, pp. 77-87 (1988); "Hydrogenolysis of 2,2-Dimethylbutane and n-Hexane over Supported Ruthenium, Nickel, Cobalt, and Iron," Machiels et al., *Journal of Catalysis*, vol. 58, pp. 268-75 (1979); "Hydrogenolysis of Saturated Hydrocarbons: Influence of Hydrocarbon Structures on the Activity and Selectivity of Nickel on Silica," Leclercq et al., *Journal of Catalysis*, vol. 99, pp. 1-11; GB 574694; U.S. Pat. Nos. 2,422,670; 2,436,923; "STRATCO Effluent Refrigerated $H_2SO_4$ Alkylation Process," in Handbook of Petroleum Refining Processes, Third Edition, Graves, ch. 1.2 (2004); "UOP Alkylene™ Process for Motor Fuel," in Handbook of Petroleum Refining Processes, Third Edition, Roeseler, ch. 1.3 (2004); and "UOP HF Alkylation Technology," in Handbook of Petroleum Refining Processes, Third Edition, Himes et al., ch. 1.2 (2004).

SUMMARY OF THE INVENTION

The present invention relates to novel processes that address the need for the production of neopentane at high yield, under mild reaction conditions, and utilizing readily available feedstock. In one aspect, the present invention relates to a process for producing neopentane comprising alkylating isobutane with butylenes to produce isooctane (2,2,4-trimethylpentane), followed by demethylating the isooctane to produce a product comprising at least 10 wt % neopentane. Typically, the butylenes can be provided in a $C_4$ olefinic feed stream, preferably a refinery raffinate stream, such as a raffinate stream obtained from cracking naphtha. In another aspect the present invention relates to a process for producing neopentane comprising demethylating isooctane to produce a product comprising at least 10 wt % neopentane.

DETAILED DESCRIPTION OF THE EMBODIMENTS

Figure 1:
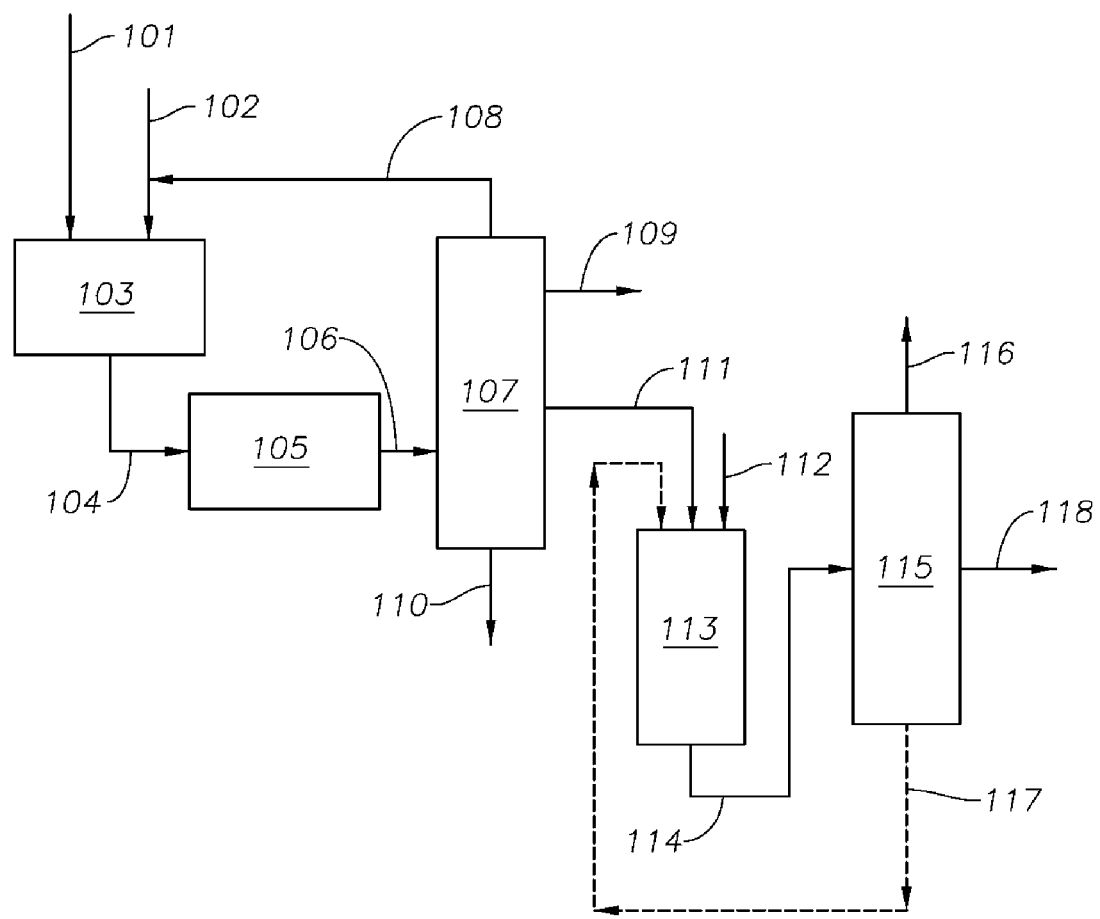
FIG. 1 is a diagram of a process of making neopentane.

Described herein are processes for producing neopentane. As discussed below, the processes involve the demethylation of isooctane, preferably via contacting the isooctane with hydrogen in the presence of a catalyst. The isooctane can be provided by the alkylation of isobutane, preferably via contacting the isobutane with butylenes in the presence of a catalyst. Preferably, the butylenes provided in a $C_4$ olefinic feed, such as a refinery raffinate stream. Alternatively, the isooctane can be provided in an independent feed stream. Preferably, the processes described herein enable the production of neopentane in quantities of greater than about 5 kg/hr, preferably greater than about 500 kg/hr, preferably greater than about 5000 kg/hr, and preferably greater than about 35000 kg/hr.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a $C_{12}$+ component" should be interpreted to include one, two or more $C_{12}$+ components unless specified or indicated by the context to mean only one specific $C_{12}$+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first feedstock are expressed based on the total weight of the first feedstock. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

As used herein, "hydrocarbon" refers to molecules or segments of molecules containing primarily hydrogen and carbon atoms. As used herein, the term "$C_n$" hydrocarbon wherein n is a positive integer, e.g., 1, 2, 3, 4, etc., means a hydrocarbon having n number of carbon atom(s) per molecule. The term "$C_n$+" hydrocarbon wherein n is a positive integer, e.g., 1, 2, 3, 4, etc., as used herein, means a hydrocarbon having at least n number of carbon atom(s) per molecule. The term "$C_n$-" hydrocarbon wherein n is a positive integer, e.g., 1, 2, 3, 4, etc., used herein, means a hydrocarbon having no more than n number of carbon atom(s) per molecule.

As used herein, "olefin" refers to any unsaturated hydrocarbon having the formula $C_nH_{2n}$ and containing one carbon-carbon double bond, wherein C is a carbon atom, H is a hydrogen atom, and n is the number of carbon atoms in the olefin.

As used herein, "alkane" or "paraffin" refers to any saturated hydrocarbon having the formula $C_nH_{2n+2}$, wherein C is a carbon atom, H is a hydrogen atom, and n is the number of carbon atoms in the alkane.

As used herein, a "primary carbon atom" refers to a carbon atom neighboring one carbon atom, "secondary carbon atom" refers to a carbon atom neighboring two carbon atoms, "tertiary carbon atom" refers to a carbon atom neighboring three carbon atoms, and "quaternary carbon atom" refers to a carbon atom neighboring four carbon atoms.

As used herein, the prefix "normal" or "n-" signifies a linear unbranched hydrocarbon.

As used herein, the prefix "iso" or "i-" signifies a hydrocarbon containing a methyl substitution at the second carbon of the hydrocarbon chain.

As used herein, the prefix "neo" signifies a hydrocarbon containing a quaternary carbon atom. For example, the term "neopentane" refers to a compound of the formula $C_5H_{12}$ and containing a quaternary carbon atom, otherwise known as 2,2-dimethylpropane.

Alkylation of Isobutane

Often, isooctane is formed in the present invention by the alkylation of isobutane, preferably via contacting the isobutane with butylenes in the presence of a catalyst. Preferably, the butylenes are provided in a $C_4$ olefinic feed stream. Suitable $C_4$ olefinic feeds include $C_4$ hydrocarbon mixtures obtained in refining, cracking (thermal, catalytic cracking or steam cracking) and/or reforming of oils, butane-butene fractions obtained by removing butadiene from $C_4$ by-product fractions formed in the production of ethylene by thermal cracking of oils, or $C_4$ hydrocarbon mixtures obtained by dehydrogenation of hydrocarbon mixtures containing n-butane and isobutane. The $C_4$ olefinic feed stream preferably comprises a raffinate stream obtained from a refinery or chemical plant cracked naphtha stream, such as from a steam cracker or fluid catalytic cracker.

Often, the $C_4$ olefinic feed comprises: from about 5 wt % to about 60 wt % isobutylene, such as from about 10 wt % to 50 wt % or about 20 wt % to 40 wt %; from about 5 wt % to about 50 wt % 1-butene, such as from about 10 wt % to 40 wt %; from about 5 wt % to about 50 wt % n-butane, such as from about 10 wt % to 40 wt % or about 20 wt % to 30 wt %; from about 5 wt % to about 50 wt % cis- and trans-2-butene, such as from about 10 wt % to 40 wt % or about 20 wt % to 30 wt %; and from about 1 wt % to about 20 wt % isobutane, such as from about 5 wt % to 10 wt %, each by weight of the olefinic feed (100 wt %). The $C_4$ olefinic feed may also have minor amounts (0.01 wt % to 5 wt %) of polar molecules or molecules comprising polar moieties such as nitriles, mercaptans, or oxygenated components. Optionally, the $C_4$ olefinic feed may further comprise butadiene.

Preferably, the alkylation is conducted in the presence of a catalyst. The catalyst employed in the alkylation reaction is generally acidic. Any catalyst suitable for isoparaffin alkylation, whether homogeneous or heterogeneous, may be used. Examples of suitable acidic homogeneous catalysts include hydrofluoric acid, sulfuric acid, and mixtures thereof. Examples of suitable acidic heterogeneous catalysts include chlorided alumina, fluorided alumina, zeolites, acidic metal oxides and mixed metal oxides, and mixtures thereof. Non-limiting examples of such zeolites include those of the MOR, BEA, FAU, MTW, and MWW families, preferably the FAU, MWW, and MOR families. Non-limiting examples of acidic metal oxides or mixed metal oxides include tungsten oxides ($WO_x$), molybdenum oxide ($MoO_x$), mixed oxides such as $WO_x/ZrO_2$, $WO_x/CeO_2$, $MoO_x/ZrO_2$, $MoO_x/CeO_2$, and sulfated zirconia.

The alkylation reaction can be conducted in a wide range of reactor configurations including fixed bed (single or in series), slurry reactors, and/or catalytic distillation towers. In addition, the alkylation reaction can be conducted in a single reaction zone or in a plurality of reaction zones, preferably in a plurality of reaction zones.

When a homogenous acid catalyst is used, such as hydrofluoric acid or sulfuric acid, suitable reaction temperatures range from about 0° C. and about 50° C., such as from about 5° C. and about 40° C., or from about 10° C. and about 25° C. In such aspects, the molar ratio of isobutane to butylenes supplied to the alkylation reaction zone or zones is typically greater than about 10:1, such as from about 10:1 to about 75:1, or from about 20:1 to about 50:1.

When a heterogeneous acid catalyst is used, such as a zeolite, suitable reaction temperatures range from about 100° C. to about 400° C., such as from about 125° C. to about 300° C., or from about 150° C. to about 250° C. In such aspects, the molar ratio of isobutane to butylenes supplied to the alkylation reaction zone or zones is typically greater than about 50:1, such as from about 50:1 to about 200:1, or from about 75:1 to about 100:1.

Irrespective of the catalyst employed, the reaction pressure is preferably maintained so that the $C_4$ olefinic feed remains in liquid form within the reactor. For instance, suitable reaction pressures are from about 100 kPa absolute to about 7000 kPa absolute (e.g., atmospheric to about 1000 psia), such as from about 500 kPa absolute to about 5000 kPa absolute.

When a homogeneous acid catalyst is employed, the alkylation reaction effluent is generally subjected to downstream treatment, preferably a water wash step, to remove entrained acid. The water wash step can be conducted in one or more stages and can be carried out in any apparatus known in the art, such as a wash tower. Optionally, the purified alkylation reaction effluent is subsequently dried. Drying may utilize a molecular sieve, such as 3 Å molecular sieves. Drying may also be accomplished by pasteurization.

Demethylation of Isooctane

The major components of the alkylation reaction effluent, whether or not subjected to downstream treatment, are generally unreacted components of the isobutane and $C_4$ olefinic feeds, primarily n-butane and isobutane, and alkylates. The alkylates typically comprise the desired product, isooctane, and a variety of $C_8+$ byproducts. The primary constituents of the alkylates, along with each of their boiling points, are summarized in Table 1.

TABLE 1

| Alkylate | Boiling Point (° C.) |
| --- | --- |
| 2,2,4-trimethyl pentane (isooctane) | 99.2 |
| 2,2,3-trimethyl pentane | 109.8 |
| 2,3,3-trimethyl pentane | 114.8 |
| 2,3,4-trimethyl pentane | 113.5 |
| 2,2,3,3-tetramethyl butane | 106.5 |
| 2-methyl-3-ethyl pentane | 115.6 |
| 3-methyl-2-ethyl pentane | 118.3 |

The unreacted feed components and alkylate byproducts can be readily removed from the reaction effluent by, for example, distillation. The remainder of the alkylation reaction effluent, mainly composed of isooctane, can be demethylated to produce neopentane. Preferably, the separated alkylation reaction effluent comprises greater than about 80 wt % isooctane, or greater than about 90 wt % isooctane, or greater than about 95 wt % isooctane, or greater than about 99 wt % isooctane, such as from about 90 wt % to about 100 wt % isooctane, or from about 95 wt % to about 99 wt % isooctane.

Alternatively or additionally, an independent isooctane feed stream can be provided and demethylated. In such aspects, the isooctane feed stream preferably comprises greater than about 80 wt % isooctane, or greater than about 90 wt % isooctane, or greater than about 95 wt % isooctane, or greater than about 99 wt % isooctane, such as from about 80 wt % to about 99 wt % isooctane, or from about 85 wt % to about 95 wt % isooctane.

In any embodiment, the isooctane feed stream preferably comprises less than about 30 wt % of aromatic hydrocarbons, such as less than about 10 wt % of aromatic hydrocarbons. Additionally or alternatively, the isooctane feed stream may be free or substantially free of aromatic hydrocarbons.

Preferably, the demethylation is conducted by contacting the isooctane with hydrogen in the presence of a catalyst. The reaction pathway for the conversion of the isooctane to neopentane typically proceeds by a step-wise demethylation that may be summarized in the following reaction scheme:

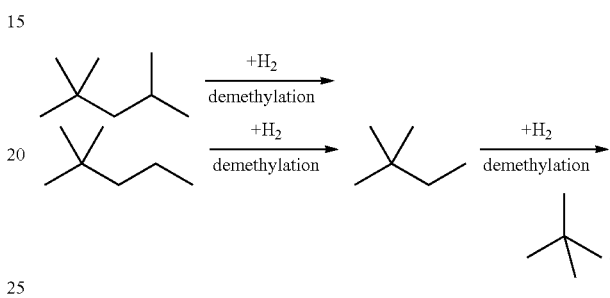

As shown from the reaction scheme above, the desired demethylation occurs at the tertiary (3°) carbon of the isooctane and the secondary (2°) carbon of the intermediates. Competing demethylation reactions can occur at the quaternary (4°) carbon. Advantageously, demethylation at the quaternary (4°) carbon in the present processes is minimized to prevent a loss of neopentane yield.

The demethylation reaction can be conducted in a wide range of reactor configurations including fixed bed (single or in series), slurry reactors, and/or catalytic distillation towers. In addition, the demethylation reaction can be conducted in a single reaction zone or in a plurality of reaction zones. The demethylation is conveniently conducted at a temperature from about 200° C. to about 500° C., such as from about 300° C. to about 400° C. and a pressure from about 100 kPa absolute to about 10000 kPa absolute (e.g., atmospheric to about 1500 psia), such as from about 300 kPa absolute to about 8000 kPa absolute, in the presence of a catalyst. Often, the demethylation is conducted at a hydrogen partial pressure of from about 50 kPa absolute to about 3500 kPa absolute (e.g., from about 7 psia to about 500 psia). Preferably, the demethylation is conducted at a hydrogen partial pressure of less than about 2500 kPa absolute, preferably less than about 2200 kPa absolute, and preferably less than about 1000 kPa absolute (e.g., preferably less than about 350 psia, or preferably less than about 150 psia). Particularly preferably, the demethylation may be conveniently conducted under conditions comprising one or more of the following: a temperature from about 220° C. to about 300° C.; a pressure from about 15 psig to about 200 psig (e.g., from about 205 kPa absolute to about 1400 kPa absolute); and a hydrogen to hydrocarbon molar ratio from about 1:1 to about 14:1.

Generally, the catalyst employed in the demethylation comprises a transition metal component. Specific, non-limiting examples of suitable transition metal components include Fe, Co, Ni, Rh, Ir, Ru, Pt, and Pd, combinations thereof, compounds thereof, and mixtures of compounds thereof, with Ni being particularly advantageous. Often, the transition metal component contains transition metal as a single component. Alternatively, the transition metal component may contain a transition metal combined with an additional metal to form a binary or ternary alloy. Specific, non-limiting examples of suitable additional metals include Cu, Au, Ag, Sn, Zn, Re, combinations thereof, compounds thereof, and mixtures of compounds thereof. Desirably, the amount of the transition metal component present in the catalyst is from about 0.05 wt % to about 60.0 wt %, such as from about 0.10 wt % to about 50.0 wt %, of the total weight of the catalyst. Generally, the transition metal component is supported on a non-acidic support material. Specific, non-limiting examples of suitable support materials include silica, theta-alumina, clay, pentasil, aluminophosphate, carbon, titania, zirconia, and mixtures thereof.

Preferably, the acidity of the catalyst employed in the demethylation is minimized to inhibit undesired cracking reactions. Often, the acidity of the catalyst is reduced via impregnation with an alkali metal compound, preferably an alkali metal hydroxide, nitrate, carbonate, bicarbonate, or oxide, such as sodium oxide, e.g., $Na_2O$. Desirably, the amount of the alkali metal compound present in the catalyst is from about 0.05 wt % to about 1.0 wt %, such as from about 0.1 wt % to about 0.5 wt %, of the total weight of the catalyst.

Typically, the overall isooctane conversion (i.e., including recycle) during the demethylation step is greater than 50%, preferably greater than 80%, preferably greater than 95%, and preferably greater than 99%, such as from 80% to 99% or 90 to 99%. The product of the demethylation step generally comprises neopentane, $C_4$− hydrocarbon components (e.g., methane, ethane, and propane) and, optionally, partially converted $C_6$+ hydrocarbon intermediate components (e.g., neohexane and neoheptane). Preferably, the product of the demethylation step comprises: at least 10 wt %, preferably at least about 25 wt %, preferably at least about 35 wt %, and ideally at least about 50 wt % of neopentane, such as from about 25 wt % to about 50 wt % or from about 30 wt % to about 40 wt %; less than about 75 wt %, preferably less than about 65 wt %, and preferably less than about 50 wt % of $C_4$− hydrocarbon components such as from about 25 wt % to about 75 wt % or from about 40 wt % to about 60 wt %; less than about 5 wt %, preferably less than about 1 wt %, and ideally less than about 0.5 wt % of non-neopentane $C_5$ hydrocarbon components, such as from about 0 wt % to about 1 wt %; and less than about 10 wt %, preferably less than about 5 wt %, preferably less than about 1 wt %, and ideally less than about 0.5 wt % of partially converted $C_6$+ hydrocarbon components (e.g., $C_6$-$C_7$ hydrocarbons), such as from about 0 wt % to about 10 wt %, or from about 0 wt % to about 1 wt %, or from about 0.5 wt % to about 1 wt %.

The light $C_4$− hydrocarbon components and the $C_6$+ hydrocarbon intermediate components can be readily removed from the demethylation product by, for example, distillation, thereby yielding a purified neopentane product stream. Preferably, the purified neopentane product stream comprises greater than about 80 wt % neopentane, or greater than about 90 wt % neopentane, or greater than about 95 wt % neopentane, or greater than about 99 wt % neopentane, such as from about 80 wt % to about 99 wt % neopentane, or from about 85 wt % to about 95 wt % neopentane.

Process

The present inventive process will now be more particularly described with reference to FIG. 1. FIG. 1 illustrates one aspect of the present inventive process, in which an isobutane stream is alkylated with butylenes provided in a $C_4$ olefinic feed stream to produce an alkylation product, after which isooctane is separated and demethylated. The invention is not limited to this aspect, and this description is not meant to foreclose other aspects within the broader scope of the invention, such as those where an independent isooctane feed stream is provided and demethylated.

As shown in FIG. 1, a $C_4$ olefinic feed stream 101 and an isobutane stream 102 are fed to an alkylation reactor 103 to produce an alkylation effluent 104 comprising isooctane, unreacted isobutane, n-butane, and alkylate byproducts, e.g., $C_8$+ hydrocarbons. Optionally, the alkylation effluent is then fed to a treatment unit(s) 105 where the alkylation product is washed with water and subsequently dried to produce a treated effluent 106. The alkylation effluent 105 or treated effluent 106 is then fed to a separator 107, e.g., a distillation column, to separate a first light fraction 108 comprising unreacted isobutane, a second light fraction 109 comprising n-butane, and a heavy fraction 110 comprising alkylate byproducts (e.g., $C_8$+ hydrocarbons) from the alkylation effluent or treated effluent. The resulting obtained fraction 111 is mainly composed of isooctane. The light fraction 108 can be recycled to alkylation reactor 103. Preferably, the light fraction 109 may be used for fuel (not shown). Preferably, the heavy fraction 110 may be used for mogas (not shown). Fraction 111 and a hydrogen stream 112 are then introduced to a demethylation reactor 113 to produce a demethylation effluent 114 comprising neopentane, $C_4$− hydrocarbons, and partially converted components, e.g., $C_6$+ hydrocarbons. The demethylation effluent 114 is then fed to a separator 115, e.g., a distillation column, to separate a light fraction 116 comprising $C_4$− hydrocarbons and a heavy fraction 117 comprising partially converted $C_6$+ hydrocarbons (primarily, $C_6$-$C_7$ hydrocarbons) from the demethylation effluent 114. The resulting obtained fraction 118 is mainly composed of neopentane. The light fraction 116 can be subjected to further downstream treatment for use as fuel (not shown). Optionally, the heavy fraction 117 can be recycled to the demethylation reactor.

Neopentane produced in accordance with the present invention is useful as a blowing agent for the production of foamed polymers and possesses several properties (e.g., a boiling point of 9.5° C. and a freezing point of −16.6° C.) making it useful as a heat removal agent and/or an inert condensing agent (ICA) in gas phase polymerization process, such as gas phase polymerization processes for the production of polyethylene. Neopentane produced in accordance with this invention also exhibits high octane numbers and is therefore useful as a gasoline blend component.

The invention will now be more particularly described with reference to the accompanying drawings and the following non-limiting Examples.

EXAMPLES

Example 1: Synthesis of 1.5% Ir/$SiO_2$ Demethylation Catalyst

A 1.5% Ir/$SiO_2$ catalyst was prepared by incipient wetness impregnation. Silica gel (Davisil™ 646, Sigma-Aldrich) was calcined by heating at a rate of 10° C./min to 700° C. and holding at 700° C. for 15 hours, then cooled to 50° C. and held at temperature overnight. The pore volume of the calcined silica was determined to be 1.34 cc/g. An aqueous solution of iridium (III) chloride was prepared by adding 0.28 g of iridium (III) chloride hydrate to 13.4 mL water, followed by adding 5 drops of concentrated HCl. The resulting mixture was then stirred and heated until the metal salt completely dissolved. The calcined silica (10 g) was then impregnated with the prepared aqueous solution to give an Ir loading of 1.5 wt %. The resultant product was transferred to a ceramic dish, calcined by heating at a rate of 10° C./min to 250° C. and holding at 250° C. for 10 hours, then cooled to 50° C. and held at temperature overnight.

Example 2: Synthesis of 1.5% Rh/SiO$_2$ Demethylation Catalyst

A 1.5% Rh/SiO$_2$ catalyst was prepared by incipient wetness impregnation. Silica gel (Davisil™ 646, Sigma-Aldrich) was calcined by heating at a rate of 10° C./min to 700° C. and holding at 700° C. for 15 hours, then cooled to 50° C. and held at temperature overnight. The pore volume of the calcined silica was determined to be 1.34 cc/g. The calcined silica (10 g) was then impregnated with a solution of rhodium (III) chloride hydrate (0.39 g) dissolved in 13.4 mL water to give an Rh loading of 1.5 wt %. The resultant product was transferred to a ceramic dish, calcined by heating at a rate of 10° C./min to 250° C. and holding at 250° C. for 10 hours, then cooled to 50° C. and held at temperature overnight.

Example 3: Synthesis of Na$_2$O/Rh/SiO$_2$ Demethylation Catalysts

Na$_2$O/Rh/SiO$_2$ catalysts with varying Na$_2$O content were prepared from the calcined 1.5% Rh/SiO$_2$ catalyst of Example 1. The 1.5% Rh/SiO$_2$ catalyst was first impregnated with an aqueous solution of NaNO$_3$ to achieve the desired Na$_2$O loading (e.g., 0.1 w % or 0.5 wt %). The Na$_2$O/Rh/SiO$_2$ catalyst was then obtained by drying the impregnated sample overnight at 100° C. followed by heating to 400° C. under flowing nitrogen.

Demethylation of Isooctane and GC Characterization Procedures for Examples 4-7

All demethylation tests described in Examples 4-7 were carried out in a down-flow, tubular, fixed bed reactor equipped with two 100-mL ISCO pumps and various gas feeds. The liquid feed was delivered via the ISCO pumps, mixed with gas feed through a heated section for vaporization before entering the reactor (⅜ in O.D.×16¾ in×0.028 in wall stainless steel tube) (1 cm×43 cm×0.07 cm). Catalyst (0.25-2 g loading) was pelletized and sized to 20-40 mesh, diluted with quartz chips to a total volume of 5 mL and loaded in the isothermal zone of the reactor. A piece of ¼ in (0.6 cm) O.D. stainless steel tubing was inserted at the bottom of the reactor tube to ensure the catalyst bed being located in the isothermal zone of the furnace. Glass wool was used at the top and bottom of the catalyst bed to keep the catalyst bed in place. Reactor pressure was controlled via a research control valve (RCV) at the exit of the reactor and the reactor effluent was heat-traced and sent to a gas chromatograph (GC) for on-line analysis.

The catalyst was first purged with N$_2$ and then heated to 300-500° C. at a ramp rate of 3° C./min under flowing H$_2$ (100 cc/min) and held 2-4 h for reduction. After reduction, the reactor was cooled down to the operating temperature. The liquid feed was then introduced and H$_2$ flow rate adjusted accordingly at the desired operating pressure.

An Agilent HP 7890 GC having a Restek 30 m×0.32 mm×5 µm GC column (Rtx™-1, Catalog #10178) was used for product analysis in Examples 4-7. The injector was set at 260° C. and the detector at 280° C. The column flow rate was 1.2 cc/min He, with typical air and H$_2$ flows for the detector. The oven temperature was programmed in the following manner: initial temperature of 40° C.; hold for 5 min; ramp at 4° C./min to 200° C.; ramp at 20° C./min to 260° C. for bake out. The total reactor effluent was sampled and analyzed hourly. GC peaks were identified using the "Alphagaz PIANO Calibration Standards" (Supelco Product #4-4586-U, available from Sigma-Aldrich) and authentic samples, using a response factor of one for all components.

Example 4: Demethylation of Isooctane Using 1.5% Ir/SiO$_2$ Catalyst

The 1.5% Ir/SiO$_2$ catalyst of Example 1 (1.019 g) was sized to 20/40 sieve mesh, dispersed with quartz chips (20/40 mesh) then loaded into the isothermal zone of the reactor to a volume of 5.5 cc. The catalyst was pre-conditioned in situ by heating to 400° C. with H$_2$ flow at 100 cc/min and holding for 2 h. The feed was mixed with hydrogen and pumped through heated lines for vaporization prior to flowing to the reactor. The feed was then pumped through the catalyst bed at initial reaction conditions comprising a temperature of 300° C. at a liquid weight hourly space velocity (LWHSV) of 4 µl, a hydrogen flow rate of 142 cc/min, and a pressure of 15 psia (100 kPa absolute).

GC testing of the reactor effluent at a temperature of 300° C. and a pressure of 15 psia yielded the following results: isooctane conversion of 30%; neoheptane selectivity of 4.8 wt %; neohexane selectivity of 4.8%; and a neopentane selectivity of 1.9 wt %.

Example 5: Demethylation of Isooctane Using Rh/SiO$_2$ Catalyst with Varying Na$_2$O Content Catalyst prepared in accordance with Example 4 (0.25-2 g, e.g., 1.049 g 0% Na$_2$O/1.5% Rb/SiO$_2$) was sized to 20/40 sieve mesh, dispersed with quartz chips (20/40 mesh) then loaded into the isothermal zone of the reactor to a volume of 5.5 cc. The catalyst was pre-conditioned in situ by heating to 400° C. with H$_2$ flow at 100 cc/min and holding for 2 h. The feed was mixed with hydrogen and pumped through heated lines for vaporization prior to flowing to the reactor. The feed was then pumped through the catalyst bed at initial reaction conditions comprising a temperature of 350° C. at a LWHSV of 4 h$^{-1}$, a hydrogen flow rate of 142 cc/min, and a pressure of 15 psia (100 kPa absolute).

The results of the GC testing of the reactor effluent at a temperature of 350° C., a pressure of 15 psia, and varying Na$_2$O content are summarized in Table 2.

TABLE 2

| Catalyst | Conversion and Selectivity | | | | | | | | | | | | |
| --- | --- | --- | --- | --- | --- | --- | --- | --- | --- | --- | --- | --- | --- |
| Na$_2$O Content (wt %) | Isooctane Conversion (%) | Methane - (wt %) | Ethane - (wt %) | Propane - (wt %) | C4 - (wt %) | Neopentane - (wt %) | Other C5 - (wt %) | Neohexane - (wt %) | Other C6 - (wt %) | Neoheptane - (wt %) | Other C7 - (wt %) | Other C8 - (wt %) | Other |
| 0 | 19.66 | 55.02 | 3.98 | 2.32 | 4.18 | 6.90 | 0.71 | 13.33 | 0.15 | 7.25 | 1.72 | 2.64 | 1.78 |
| 0.1 | 19.93 | 59.60 | 3.64 | 2.13 | 3.77 | 7.99 | 0.58 | 11.76 | 0.12 | 5.77 | 1.43 | 1.91 | 1.32 |
| 0.5 | 19.89 | 64.56 | 2.82 | 1.80 | 3.68 | 9.01 | 0.47 | 9.20 | 0.07 | 4.42 | 1.07 | 1.65 | 1.25 |

Table 2 illustrates that the selectivity towards neopentane increased with increasing $Na_2O$ content. This result was likely attributable to the titration effect of the $Na_2O$ on residual acidity of the $Rb/SiO_2$ catalyst.

Example 6: Demethylation of Isooctane Using $Rh/SiO_2$ Catalyst with Varying Reaction Pressure The demethylation kinetics of isooctane at a variety of reaction pressures was measured by comparing the rate of the desired demethylation of the tertiary carbon, r(3° C.), to the rate of the undesired demethylation of the quaternary carbon, r(4° C.) [r(3° C.)/r(4° C.)] in accordance with the following procedure.

The $Rb/SiO_2$ catalyst of Example 2 (0 wt % $Na_2O$ content) was loaded and pre-conditioned in accordance with Example 5. At each of the reaction pressures tested, the isooctane feed was pumped through the catalyst bed at a variety of flow rates in order to vary the residence time of the feed within the reactor. The r(3° C.)/r(4° C.) ratio was obtained by comparing the selectivity of the primary demethylation product at the varied residence times and extrapolating these results to a zero residence time. The results of the kinetics measurements are summarized in Table 3.

TABLE 3

| Pressure (psia) | Pressure (kPa absolute) | r(3° C.)/r(4° C.) |
| --- | --- | --- |
| 30 | 200 | 8.5 |
| 115 | 800 | 2.5 |
| 315 | 2000 | 1.3 |

Table 3 illustrates that the r(3° C.)/r(4° C.) ratio decreased with increasing reactor pressure. This result indicates that a low reaction pressure is desirable to obtain the desired neopentane product.

Example 7: Demethylation of Isooctane Using Ni/Kieselguhr Catalyst with Varying Isooctane Flow Rate A Ni/Kieselguhr catalyst (60% Ni, Sigma-Aldrich) (2.066 g) was sized to 20/40 sieve mesh, dispersed with quartz chips (20/40 mesh) then loaded into the isothermal zone of the reactor to a volume of 5.5 cc. The catalyst was pre-conditioned in situ by heating to 500° C. with $H_2$ flow at 100 cc/min and holding for 4 h. The feed was mixed with hydrogen and pumped through heated lines for vaporization prior to flowing to the reactor. The feed was then pumped through the catalyst bed at initial reaction conditions comprising a temperature of 250° C. at LWHSV of 1 h$^{-1}$ or 2 h$^{-1}$, a hydrogen flow rate of 71 cc/min, and a pressure of 15 psia (100 kPa absolute).

Typical results of the GC testing of the reactor effluent at a temperature of 250° C. and a pressure of 15 psia are summarized in Table 4. In addition, the conversion of isooctane and selectivity to neopentane, neohexane, and neoheptane against T.O.S. at the two tested isooctane flow rates are shown in FIG. 2.

TABLE 4

| Isooctane Flow Rate LWHSV (h$^{-1}$) | Isooctane Conversion (%) | Methane - (wt %) | Ethane - (wt %) | Propane - (wt %) | C4 - (wt %) | Neopentane - (wt %) | Other C5 - (wt %) | Neohexane - (wt %) | Other C6 - (wt %) | Neoheptane - (wt %) | Other C7 - (wt %) |
| --- | --- | --- | --- | --- | --- | --- | --- | --- | --- | --- | --- |
| 1 | 100 | 47.7 | 3.5 | 4.3 | 2.3 | 40.4 | 0 | 1.8 | 0 | 0 | 0 |
| 2 | 99.9 | 30.7 | 1.0 | 1.1 | 3.3 | 15.9 | 1.9 | 37.4 | 0.3 | 7.4 | 0.9 |

Figure 2:
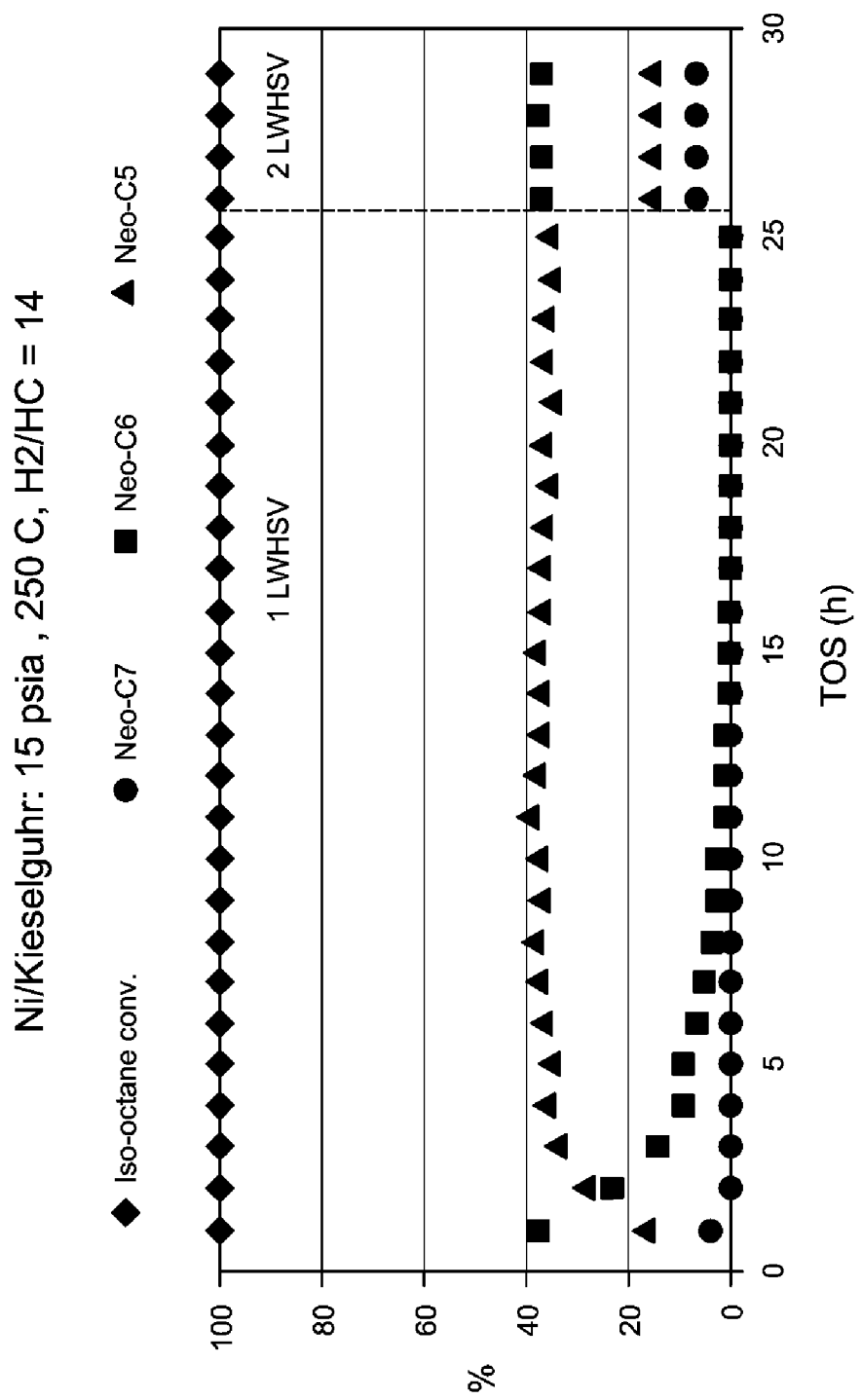
FIG. 2 is a graph of conversion of isooctane to neopentane, neohexane, and neoheptane against time on stream (T.O.S.) in the demethylation of Example 7.

Table 4 and FIG. 2 illustrate that the selectivity towards neopentane decreased with increasing isooctane flow rate. Conversely, the selectivity towards neohexane and other $C_6+$ hydrocarbons increased with increasing isooctane flow rate. These results indicate that at high isooctane flow rate (i.e., short residence time) the step-wise demethylation of isooctane to neopentane did not run to completion and intermediate products were obtained.

Example 8: Demethylation of Isooctane Using $Ni/SiO_2$ Catalyst with Varying Process Conditions The demethylation tests described in Examples 8A-8M were carried out in a reactor unit having eight modules serviced by communal gas and liquid feed lines. Each individual module featured independent temperature, pressure, and feed flow controls.

A $Ni/SiO_2$ catalyst (64 wt % Ni powder on silica, obtained from Strem Chemicals, Inc.) was pelletized, crushed, sieved (40-20 mesh, 840 to 400 μm), and loaded into each of the unit modules along with SiC diluent. The catalyst loading amount was varied depending on the desired WHSV of the isooctane feed. The catalyst was pre-conditioned in situ by heating to 400° C. with $H_2$ flow at 500 sccm/min at 30 psig (300 kPa absolute) and holding for 8 h.

An Agilent HP 7890 GC equipped with dual inlets (i.e., a front inlet and a rear inlet), two FID detectors, and two 60 m×250 μm×1.0 μm HP-1 GC columns (Agilent Technologies) located in parallel (corresponding to the front inlet and rear inlet, respectively) was used for online product analysis to determine the reported conversion and selectivity values. Modules 1-4 of the reactor unit were connected in series with the front inlet, and modules 5-8 of the reactor unit were connected to the rear inlet. Sample injection was enabled via a 250 μl sample loop that was connected to a Valco 6 port GC injection valve. In order to increase the sampling frequency, two simultaneous injections were done for both inlets.

The GC was operated in a ramped pressure and split mode using hydrogen as carrier gas and a split ratio of 100 to 1. The initial pressure was set at 20 psi (140 kPa) and held for 1.5 min, and then ramped at 7 psi/min (50 kPa/min) to a final pressure of 50 psi (340 kPa). The initial oven temperature was set at 35° C. and held for 2 min, and then ramped at 25° C./min to 250° C. The total analysis time was about 10.6 min, which enabled an injection every 15 min and a corresponding analysis frequency of 1 h per pair of modules.

In each of examples 8A-8M, the WHSV of the isooctane feed was varied in order to vary the residence time of the feed within the reactor. Results of the GC testing at varying process conditions (temperature, total pressure, hydrogen to hydrocarbon ($H_2$:HC) molar ratio, and WHSV) are summarized in Table 5.

TABLE 5

| | Process Conditions | | | | Conversion and Selectivity | | | | | |
|---|---|---|---|---|---|---|---|---|---|---|
| Example | Temperature (° C.) | Total pressure (psig) | H2:HC (mol:mol) | WHSV (h−1) | Isooctane Conversion (%) | Neoheptane Selectivity (% mol) | 2,4-dimethylpentane Selectivity (% mol) | Neohexane Selectivity (% mol) | 2-methylpentane Selectivity (% mol) | Neopentane Selectivity (% mol) | Isopentane Selectivity (% mol) |
| 8A | 220 | 150 | 8 | 0.45 | 22.25 | 29.50 | 6.04 | 6.68 | 1.18 | 0.22 | 0.16 |
| | | | | 1.1 | 4.66 | 37.68 | 7.17 | 2.54 | 0.30 | 0.00 | 0.00 |
| | | | | 2 | 8.63 | 35.61 | 6.81 | 3.54 | 0.50 | 0.07 | 0.00 |
| | | | | 12 | 0.77 | 46.93 | 7.66 | 2.75 | 0.00 | 0.00 | 0.00 |
| 8B | 230 | 100 | 14 | 0.5 | 61.23 | 18.57 | 2.22 | 12.54 | 1.80 | 1.37 | 0.84 |
| | | | | 0.75 | 50.33 | 22.84 | 2.94 | 10.96 | 1.74 | 0.73 | 0.48 |
| | | | | 1 | 58.58 | 19.66 | 2.94 | 11.84 | 2.02 | 1.09 | 0.73 |
| | | | | 1.5 | 38.24 | 26.61 | 4.01 | 8.65 | 1.54 | 0.45 | 0.29 |
| | | | | 2 | 29.35 | 29.32 | 4.43 | 7.17 | 1.19 | 0.31 | 0.19 |
| | | | | 5 | 11.45 | 34.84 | 5.31 | 4.55 | 0.60 | 0.13 | 0.00 |
| 8C | 235 | 32 | 5 | 2 | 51.00 | 20.03 | 0.53 | 13.52 | 0.59 | 1.80 | 0.43 |
| | | | | 4 | 79.68 | 14.83 | 0.30 | 15.91 | 0.69 | 2.49 | 0.63 |
| 8D | 235 | 100 | 14 | 0.5 | 64.75 | 18.07 | 1.91 | 13.06 | 1.75 | 1.60 | 0.86 |
| | | | | 1 | 73.90 | 14.99 | 1.93 | 14.06 | 2.20 | 1.61 | 1.05 |
| | | | | 2 | 44.03 | 27.30 | 3.78 | 10.40 | 1.58 | 0.59 | 0.40 |
| | | | | 3 | 31.27 | 29.16 | 4.06 | 7.51 | 1.27 | 0.34 | 0.21 |
| | | | | 4 | 41.16 | 27.51 | 3.15 | 9.74 | 1.12 | 1.46 | 0.66 |
| | | | | 5 | 27.52 | 30.05 | 3.80 | 7.38 | 1.16 | 0.33 | 0.19 |
| 8E | 240 | 32 | 5 | 2 | 68.08 | 15.05 | 0.27 | 16.13 | 0.48 | 2.75 | 0.53 |
| | | | | 4 | 82.45 | 13.67 | 0.22 | 16.25 | 0.51 | 3.13 | 0.57 |
| 8F | 240 | 100 | 3 | 1 | 28.14 | 29.78 | 1.74 | 9.86 | 0.49 | 0.48 | 0.16 |
| | | | | 2 | 31.08 | 28.64 | 1.82 | 10.11 | 0.61 | 0.53 | 0.18 |
| | | | | 3 | 26.90 | 31.27 | 2.02 | 8.83 | 0.58 | 0.43 | 0.14 |
| | | | | 4 | 11.03 | 30.25 | 1.84 | 5.66 | 0.33 | 0.28 | 0.13 |
| | | | | 6 | 13.03 | 35.57 | 2.41 | 6.39 | 0.35 | 0.29 | 0.06 |
| | | | | 15 | 23.42 | 31.10 | 2.80 | 7.56 | 0.85 | 0.37 | 0.17 |
| 8G | 240 | 100 | 4 | 1 | 54.98 | 21.85 | 1.25 | 13.62 | 0.85 | 1.38 | 0.50 |
| | | | | 3 | 47.47 | 25.13 | 2.12 | 10.85 | 1.35 | 0.74 | 0.42 |
| | | | | 6 | 18.23 | 34.31 | 2.42 | 6.98 | 0.44 | 0.30 | 0.08 |
| | | | | 15 | 19.29 | 32.48 | 3.10 | 6.85 | 0.74 | 0.31 | 0.13 |
| 8H | 240 | 100 | 5 | 1.2 | 44.20 | 25.02 | 1.79 | 11.98 | 0.88 | 0.67 | 0.29 |
| | | | | 1.22 | 69.68 | 17.48 | 1.14 | 15.49 | 1.22 | 1.32 | 0.61 |
| | | | | 2.7 | 31.45 | 28.10 | 2.24 | 7.97 | 0.66 | 0.37 | 0.15 |
| | | | | 4 | 72.63 | 17.43 | 1.38 | 14.10 | 1.78 | 1.46 | 0.82 |
| | | | | 5 | 44.05 | 26.22 | 2.24 | 10.12 | 1.25 | 0.69 | 0.38 |
| | | | | 30 | 8.12 | 35.87 | 3.77 | 4.98 | 0.40 | 0.19 | 0.05 |
| 8I | 240 | 100 | 14 | 0.5 | 92.91 | 4.28 | 0.35 | 13.28 | 0.72 | 6.58 | 1.83 |
| | | | | 1 | 68.35 | 17.34 | 2.04 | 12.86 | 2.01 | 1.61 | 0.94 |
| | | | | 1.5 | 77.74 | 14.57 | 1.60 | 14.36 | 2.20 | 1.70 | 1.08 |
| | | | | 2 | 65.59 | 19.17 | 2.21 | 12.54 | 2.06 | 1.08 | 0.72 |
| | | | | 3 | 47.15 | 25.11 | 3.10 | 9.70 | 1.57 | 0.55 | 0.38 |
| | | | | 5 | 30.57 | 29.11 | 3.76 | 7.70 | 1.28 | 0.36 | 0.22 |
| | | | | 7.5 | 14.32 | 40.94 | 4.74 | 6.68 | 0.76 | 0.24 | 0.08 |
| 8J | 240 | 150 | 8 | 0.45 | 99.83 | 0.37 | 0.03 | 8.80 | 0.30 | 10.04 | 2.05 |
| | | | | 1.1 | 59.08 | 17.49 | 2.70 | 10.77 | 1.35 | 2.71 | 1.05 |
| | | | | 2 | 48.53 | 22.31 | 3.45 | 10.73 | 1.72 | 0.93 | 0.61 |
| | | | | 12 | 5.38 | 47.77 | 6.76 | 4.52 | 0.39 | 0.10 | 0.00 |
| 8K | 247 | 100 | 14 | 3 | 79.34 | 14.90 | 1.30 | 14.38 | 2.09 | 1.74 | 1.05 |
| | | | | 4 | 67.44 | 19.18 | 1.82 | 12.77 | 1.98 | 1.17 | 0.73 |
| | | | | 6 | 50.85 | 24.42 | 2.52 | 10.36 | 1.68 | 0.69 | 0.43 |
| 8L | 255 | 100 | 14 | 0.5 | 57.93 | 21.05 | 1.53 | 11.19 | 1.34 | 1.59 | 0.77 |
| | | | | 1.5 | 78.04 | 16.08 | 1.22 | 13.39 | 2.10 | 1.45 | 1.05 |
| | | | | 2 | 66.89 | 20.23 | 1.72 | 11.72 | 2.04 | 0.96 | 0.74 |
| | | | | 3 | 50.14 | 25.33 | 2.46 | 9.31 | 1.76 | 0.55 | 0.44 |
| | | | | 5 | 77.34 | 14.58 | 0.97 | 14.17 | 1.69 | 2.25 | 1.06 |
| | | | | 10 | 51.63 | 23.20 | 1.96 | 10.92 | 1.59 | 0.98 | 0.53 |
| | | | | 15 | 36.42 | 27.35 | 2.48 | 9.03 | 1.29 | 0.65 | 0.33 |
| | | | | 20 | 29.54 | 29.15 | 2.73 | 8.11 | 1.13 | 0.55 | 0.25 |
| 8M | 267 | 100 | 14 | 15 | 77.09 | 14.97 | 0.73 | 13.81 | 1.47 | 2.49 | 0.98 |
| | | | | 20 | 66.92 | 18.43 | 1.01 | 12.85 | 1.49 | 1.85 | 0.79 |
| | | | | 30 | 47.47 | 24.00 | 1.61 | 10.64 | 1.40 | 1.09 | 0.50 |

From the data obtained in Examples 8A-8M, the absolute rates of the reactions producing the primary demethylation products and the relative rates of these reactions compared to others were regressed by comparing the selectivity of the demethylation products at the varied residence times and extrapolating these results to a zero residence time. The regressed absolute and relative reaction rates were then used to calculate simulated neopentane yields and production rates at a conversion of 80% in a theoretical demethylation process comprising demethylating an isooctane feed and recycling the produced $C_6+$ hydrocarbon fraction. The obtained simulated neopentane yields and ratios of the simulated neopentane production rates relative to the simulated neopentane production rate of Example 8A at varying process conditions (temperature, total pressure, and hydrogen to hydrocarbon ($H_2$:HC) molar ratio) are summarized in Table 6.

TABLE 6

| Example | Temperature (° C.) | Pressure (psig) | H2:HC (mol:mol) | Simulated Neopentane Yield at 80% Conversion | Ratio of Simulated Neopentane Production Rate Relative to Simulated Neopentane Rate of Example 8A at 80% Conversion |
|---|---|---|---|---|---|
| 8A | 220 | 150 | 8 | 47 | 1.0 |
| 8B | 230 | 100 | 14 | 49 | 2.4 |
| 8C | 235 | 32 | 5 | 53 | 14.7 |
| 8D | 235 | 100 | 14 | 49 | 3.3 |
| 8E | 240 | 32 | 5 | 55 | 20.0 |
| 8F | 240 | 100 | 3 | 52 | 9.9 |
| 8G | 240 | 100 | 4 | 52 | 8.0 |
| 8H | 240 | 100 | 5 | 50 | 7.0 |
| 8I | 240 | 100 | 14 | 49 | 4.5 |
| 8J | 240 | 150 | 8 | 47 | 3.5 |
| 8K | 247 | 100 | 14 | 50 | 6.9 |
| 8L | 255 | 100 | 14 | 51 | 11.0 |
| 8M | 267 | 100 | 14 | 51 | 21.5 |

As can be seen from Table 6, the simulated neopentane production rates varied significantly with changing process conditions, as expected. However, despite the wide variance in the simulated neopentane production rates, the simulated neopentane yield at 80% remained surprisingly near constant with respect to variances in each of temperature, pressure, and $H_2$:HC ratio. These simulated results suggest that the demethylation step is surprisingly robust over the preferred process conditions comprising a temperature from about 220° C. to about 300° C.; a pressure from about 15 psig to about 200 psig (e.g., from about 205 kPa absolute to about 1400 kPa absolute); and/or a hydrogen to hydrocarbon molar ratio from about 1:1 to about 14:1.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for producing neopentane, the process comprising:
    (a) contacting isobutane with butylenes under alkylation conditions effective to produce an alkylation product comprising isooctane; and
    (b) demethylating the isooctane by contacting the isooctane with hydrogen at a temperature of from 200 to 500° C., a hydrogen partial pressure of about 7 psia to about 500 psia, and in the presence of a catalyst comprising at least one member selected from the group consisting of Fe, Co, Ni, Rh, Jr, Ru, Pt, Pd, combinations thereof, compounds thereof, and mixtures of compounds thereof, to produce a demethylation product comprising at least 10 wt % neopentane based on the weight of the demethylation product, wherein the catalyst further comprises at least one member selected from the group consisting of Cu, Au, Ag, Sn, Zn, Re, combinations thereof, compounds thereof, and mixtures of compounds thereof.

2. The process of claim 1, wherein at least part of the isooctane is separated from the alkylation product prior to demethylation.

3. The process of claim 2, wherein separating the isooctane from the alkylation product comprises distillation.

4. The process of claim 3, wherein the alkylation product is separated into fractions comprising (1) an unreacted isobutane fraction, (2) an isooctane fraction, and (3) a non-isooctane $C_{8+}$ hydrocarbon fraction.

5. The process of claim 4, wherein the contacting is carried out in a reaction vessel, and wherein the unreacted isobutane fraction is recycled to the reaction vessel.

6. The process of claim 1, wherein the butylenes are provided in a raffinate stream obtained from cracking a naphtha stream.

7. The process of claim 1, wherein the contacting is carried out in the presence of a catalyst (A) comprising sulfuric acid, hydrofluoric acid, or mixtures thereof.

8. The process of claim 7, further comprising washing the alkylation product with water.

9. The process of claim 7, wherein the contacting is carried out at a temperature ranging from about 0° C. to about 50° C. and wherein the molar ratio of isobutane to butylenes supplied to the contacting ranges from about 10:1 to about 75:1.

10. The process of claim 1, wherein the contacting is carried out in the presence of a catalyst (B) selected from the group consisting of chlorided alumina, fluorided alumina, acidic metal oxide, acidic mixed metal oxide, zeolites, and mixtures thereof.

11. The process of claim 10, wherein the contacting is carried out at a temperature ranging from about 100° C. to about 400° C. and wherein the molar ratio of isobutane to butylenes supplied to the contacting ranges from about 50:1 to about 200:1.

12. The process of claim 1, further comprising separating at least part of the neopentane from the demethylation product.

13. The process of claim 12, wherein separating the neopentane from the demethylation product comprises distillation.

14. The process of claim 13, wherein the demethylation product is separated into fractions comprising (1) a $C_{4-}$ hydrocarbon fraction, (2) a neopentane fraction, and (3) a $C_{6+}$ hydrocarbon fraction.

15. The process of claim 14, wherein the demethylation is carried out in a reaction vessel, and wherein the $C_{6+}$ hydrocarbon fraction is recycled to the reaction vessel.

16. The process of claim 1, wherein the catalyst (C) comprises a support material selected from the group consisting of silica, theta-alumina, clay, pentasil, aluminophosphate, carbon, titania, zirconia, and mixtures thereof.

17. The process of claim 1, wherein the demethylation is carried out under conditions comprising at least one of a temperature from about 220° C. to about 300° C., a pressure from about 15 psig to about 200 psig (about 205 kPa absolute to about 1400 kPa absolute), or a hydrogen to hydrocarbon molar ratio from about 1:1 to about 14:1.

18. The process of claim 1, wherein the demethylation product comprises from about 25 wt % to about 50 wt % neopentane based on the weight of the demethylation product and from about 0 wt % to about 10 wt % $C_{6+}$ hydrocarbon components based on the weight of the demethylation product.

19. A process for producing neopentane, the process comprising:
(a) providing a stream comprising isooctane; and
(b) demethylating the isooctane by contacting the isooctane with hydrogen at a temperature of from 200 to 500° C., a hydrogen partial pressure of about 7 psia to about 500 psia, and in the presence of a catalyst comprising at least one member selected from the group consisting of Fe, Co, Ni, Rh, Ir, Ru, Pt, Pd, combinations thereof, compounds thereof, and mixtures of compounds thereof, to produce a demethylation product comprising at least 10 wt % neopentane based on the weight of the demethylation product, wherein the catalyst further comprises at least one member selected from the group consisting of Cu, Au, Ag, Sn, Zn, Re, combinations thereof, compounds thereof, and mixtures of compounds thereof.

* * * * *